United States Patent
Bay et al.

(10) Patent No.: US 10,875,826 B2
(45) Date of Patent: *Dec. 29, 2020

(54) PROCESS FOR THE MANUFACTURE OF SNAC (SALCAPROZATE SODIUM)

(75) Inventors: William Elliot Bay, Ridgefield, CT (US); Joseph Norman Bernadino, Stamford, CT (US); George Frederick Klein, Tarrytown, NY (US); Yi Ren, Warren, NJ (US); Pingsheng Zhang, Florence, SC (US)

(73) Assignee: Emisphere Technologies, Inc., Roseland, NJ (US)

(*) Notice: Subject to any disclaimer, the term of this patent is extended or adjusted under 35 U.S.C. 154(b) by 3756 days.

This patent is subject to a terminal disclaimer.

(21) Appl. No.: 16/490,424

(22) PCT Filed: Aug. 30, 2007

(86) PCT No.: PCT/EP2007/059037
§ 371 (c)(1),
(2), (4) Date: Aug. 30, 2019

(87) PCT Pub. No.: WO2008/028859
PCT Pub. Date: Mar. 13, 2008

(65) Prior Publication Data
US 2020/0071263 A1    Mar. 5, 2020

Related U.S. Application Data

(60) Provisional application No. 60/842,775, filed on Sep. 7, 2006.

(51) Int. Cl.
| C07C 231/10 | (2006.01) |
| C07C 231/24 | (2006.01) |
| C07C 231/12 | (2006.01) |

(52) U.S. Cl.
CPC .......... *C07C 231/10* (2013.01); *C07C 231/12* (2013.01); *C07C 231/24* (2013.01)

(58) Field of Classification Search
CPC .... C07C 231/10; C07C 231/24; C07C 235/60
See application file for complete search history.

(56) References Cited

U.S. PATENT DOCUMENTS

| 3,840,570 | A | 10/1974 | Julian |
| 4,927,814 | A | 5/1990 | Gall et al. |
| 5,650,386 | A | 7/1997 | Leone-Bay et al. |
| 5,717,109 | A | 2/1998 | Arnold et al. |
| 6,221,583 | B1 | 4/2001 | Kayyem et al. |
| 6,949,577 | B2 | 9/2005 | Allerton et al. |
| 7,056,669 | B2 | 6/2006 | Kayyem et al. |
| 7,119,073 | B2 | 10/2006 | Colarusso et al. |
| 7,125,668 | B2 | 10/2006 | Kayyem et al. |
| 7,323,460 | B2 | 1/2008 | Egbertson et al. |
| 7,381,525 | B1 | 6/2008 | Kayyem et al. |
| 7,393,645 | B2 | 7/2008 | Kayyem et al. |
| 7,524,813 | B2 | 4/2009 | Zundel et al. |
| 7,544,833 | B2* | 6/2009 | Bay .................. C07C 231/10 560/39 |
| 7,550,494 | B2 | 6/2009 | Wu et al. |
| 7,705,142 | B2 | 4/2010 | Reddy et al. |
| 8,198,448 | B2 | 6/2012 | Albrecht et al. |
| 8,212,041 | B2 | 7/2012 | Albrecht et al. |
| 8,217,177 | B2 | 7/2012 | Albrecht et al. |
| 8,258,312 | B2 | 9/2012 | Tyagi et al. |
| 8,338,471 | B2 | 12/2012 | Wallberg et al. |
| 8,372,875 | B2 | 2/2013 | Kerns |
| 8,809,258 | B2 | 8/2014 | Kajihara et al. |
| 9,272,992 | B2 | 3/2016 | Li et al. |
| 9,518,008 | B2 | 12/2016 | Van Nieuwenhze et al. |
| 2006/0173046 | A1 | 8/2006 | Bell et al. |
| 2008/0188460 | A1 | 8/2008 | Casara et al. |
| 2009/0253166 | A1 | 10/2009 | Zundel et al. |
| 2009/0264425 | A1 | 10/2009 | Jones et al. |
| 2012/0022056 | A1 | 1/2012 | Bentley et al. |

(Continued)

FOREIGN PATENT DOCUMENTS

| WO | 1997010197 A1 | 3/1997 |
| WO | 1999014238 A1 | 3/1999 |
| WO | 2000046182 A1 | 8/2000 |

(Continued)

OTHER PUBLICATIONS

Protease-catalyzed synthesis of Bz-Arg-Gly-Asp-OMe in full aqueous medium; Hou, Rui-zhen; Li, Hong-mei; Liu, Yun-iia; Zhang, Long; Xu, Li; Zhang, Xue-zhong; Chemical Research in Chinese Universities (2007), 23(6), 693-696.

Vanchrobactin: absolute configuration and total synthesis; Soengas, Raquel G.; Anta, Cristina; Espada, Alfonso; Nieto, Rosa M.; Larrosa, Marta; Rodriguez, Jaime; Jimenez, Carlos; Tetrahedron Letters (2007), 48(17), 3021-3024.

Glycoconjugate Nanoribbons from the Self-Assembly of Carbohydrate-Peptide Block Molecules for Controllable Bacterial Cell Cluster Formation; Lim, Yong-beom; Park, Somi; Lee, Eunji; Jeong, Haemi; Ryu, Ja-Hyoung; Lee, Myeong Sup; Lee, Myongsoo; Biomacromolecules (2007), 8(5), 1404-1408.

Multi-enzyme one-pot strategy for the synthesis of sialyl Lewis X-containing PSGL-1 glycopeptide; Huang, Kuo-Ting; Wu, Bing-Ching; Lin, Chang-Ching; Luo, Shih-Chi; Chen, Chinpan; Wong, Chi-Huey; Lin, Chun-Cheng; Carbohydrate Research (2006), 341(12), 2151-2155.

Enzymatic synthesis of a CCK-8 tripeptide fragment; Xiang, Hua; Eckstein, Heiner; Chinese Journal of Chemistry (2004), 22(10), 1138-1141.

(Continued)

*Primary Examiner* — Jafar F Parsa
(74) *Attorney, Agent, or Firm* — Morgan, Lewis & Bockius LLP

(57) ABSTRACT

Disclosed are improved methods for the synthesis of N-(8-[2-hydroxybenzoyl]-amino) caprylic acid. Certain compounds have been found useful for preventing the formation of a colored impurity when included in an ester hydrolysis reaction. Conducting ester hydrolysis in anaerobic conditions has also been found to minimize the formation of the color impurity. Also disclosed are improved methods for synthesizing the sodium salt of N-(8-[2-hydroxybenzoyl]-amino) caprylic acid.

14 Claims, No Drawings

(56) References Cited

U.S. PATENT DOCUMENTS

2014/0235822 A1  8/2014  Kajihara et al.

FOREIGN PATENT DOCUMENTS

| WO | 2000059863 | A1 | 10/2000 |
|---|---|---|---|
| WO | 2001070219 | A1 | 10/2001 |
| WO | 2001092206 | A1 | 12/2001 |
| WO | 2005107462 | A2 | 11/2005 |

OTHER PUBLICATIONS

Total enzymatic synthesis of cholecystokinin CCK-5; Xiang, H.; Xiang, G. Y.; Lu, Z. M.; Guo, L.; Eckstein, H.; Amino Acids (2004), 27(1), 101-105.

Second-generation lymphocyte function-associated antigen-1 inhibitors: 1H-imidazo[1,2-☐]imidazol-2-one derivatives; Emeigh, Jonathan; Gao, Donghong A.; Goldberg, Daniel R.; Kuzmich, Daniel; Miao, Clara; Potocki, Ian; Qian, Kevin C.; Sorcek, Ronald J.; Jeanfavre, Deborah D.; Kishimoto, Kei; Mainolfi, Elizabeth A.; Nabozny, Gerald, Jr.; Reilly, Patricia; Rothlein, Robert; Sellati, Rosemarie H.; Woska, Joseph R., Jr.; Chen, Shirlynn; Gunn, Jocelyn A.; O'Brien, Drane; Norris, Stephen H.; Kelly, Terence A.; Peng, Charline; Wu, Jiang-Ping; Journal of Medicinal Chemistry (2004).

Synthesis and Activities of Pyoverdin-Quinolone Adducts: A Prospective Approach to a Specific Therapy Against Pseudomonas aeruginosa; Hennard, Christophe; Truong, Que Chi; Desnottes, Jean-Francois; Paris, Jean-Marc; Moreau, Nicole J.; Abdallah, Mohamed A.; Journal of Medicinal Chemistry (2001), 44(13), 2139-2151.

Design and synthesis of novel tubular and cage structures based on thiazole-containing macrolactams related to marine cyclopeptides; Pattenden, Gerald; Thompson, Toby; Chemical Communications (Cambridge, United Kingdom) (2001), (8), 717-718.

Chemoenzymatic synthesis of structured triacylglycerols containing eicosapentaenoic and docosahexaenoic acids; Haraldsson, Gudmundur G.; Halldorsson, Amar; Kulas, Elin; Journal of the American Oil Chemists' Society (2000), 77(11), 1139-1145.

Design and Synthesis of Pyrrolidine-5,5-trans-lactams 5-Oxo-hexahydro-pyrrolo[3,2-b]pyrroles) as Novel Mechanism-Based Inhibitors of Human Cytomegalovirus Protease. 1. The ☐-Methyl-trans-lactam Template; Borthwick, Alan D.; Angier, S. Jane; Crame, Andrew J.; Exall, Anne M.; Haley, Terry M.; Hart, Graham J.; Mason, Andrew M.; Pennell, Andrew M. K.; Weingarten, Gordon G.; Journal of Medicinal Chemistry (2000), 43(23), 4452-4464.

Quinolizidines. XXII. An extension of the "3-acetylpyridine route" to the syntheses of 9-hydroxy-10-methoxy- and 10-hydroxy-9-methoxybenzo[a]quinolizidine-type Alangium alkaloids; Fujii, Tozo; Ohba, Masashi; Sakaguchi, Jun; Chemical & Pharmaceutical Bulletin (1987), 35(9), 3628-40.

* cited by examiner

PROCESS FOR THE MANUFACTURE OF SNAC (SALCAPROZATE SODIUM)

CROSS-REFERENCE TO RELATED APPLICATIONS

This application is a U.S. national phase application under 35 U.S.C. § 371 of International Application No. PCT/EP2007/059037 filed Aug. 30, 2007, which claims the benefit of U.S. Provisional Application No. 60/842,775, filed Sep. 7, 2006, and are hereby incorporated by reference in their entirety.

The present invention provides new methods for the synthesis of N-(8-[2-hydroxybenzoyl]-amino) caprylic acid and and its sodium salts.

General preparations of N-(8-[2-hydroxybenzoyl]-amino) caprylic acid (SNAC) are set out in U.S. Pat. No. 5,650,386 and International Publication Nos. WO 00/46182 and WO 00/59863.

The term "SNAC" as used herein refers to N-(8-[2-hydroxybenzoyl]-amino) caprylic acid and pharmaceutically acceptable salts thereof, including its monosodium and disodium salts. The term "SNAC free acid" refers to N-(8-[2-hydroxybenzoyl]-amino) caprylic acid. Unless otherwise noted, the term "SNAC" refers to all forms of SNAC, including all amorphous and polymorphic forms of SNAC, such as SNAC trihydrate and those described in U.S. Ser. Nos. 60/619,418 and 60/569,476, both of which, to the extent necessary, are hereby incorporated by reference.

The term "therapeutically effective amount" with respect to a bisphosphonate means an amount of the compound, or a pharmaceutically acceptable salt thereof, which is effective to treat, prevent, alleviate or ameliorate symptoms of disease, either alone or in combination with a carrier, such as SNAC.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean a range of up to 10%, preferably up to 5%.

The term "an amount effective to facilitate absorption of the bisphosphonate in the gastrointestinal tract such that the bisphosphonate is therapeutically effective" as applied to SNAC or its salts means an amount of the carrier that increases absorption of the bisphosphonate in the gastrointestinal tract such as to reduce the amount of bisphosphonate as compared to the amount of bisphosphonate required if administered alone to achieve a therapeutic effect.

The term "bisphosphonate is present in an amount not therapeutically effective when the bisphosphonate is orally administered alone" means an amount of a bisphosphonate, or a pharmaceutically acceptable salt thereof, which is not effective to treat, prevent, alleviate or ameliorate symptoms of disease. For example, the therapeutically effective amount of ibandronate for the treatment of osteoporosis is 2.5 mg daily or 150 mg monthly, as measured by the weight of the free acid. Amounts of ibandronate less than the above, for their respective dosage periods, would not be considered therapeutically effective. "[W]hen the bisphosphonate is orally administered alone" means when the bisphosphonate is not orally administered with an agent that facilitates absorption of the bisphosphonate in the gastrointestinal tract.

This term does not exclude conventional additives normally included in such formulations including, but not limited to, lactose monohydrate, croscarmellose sodium, povidone, water, sodium stearyl fumarate, and the like. Preferred oral dosage forms are tablets, most preferably tablets containing povidone.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hygroscopicity, and solubility of compounds. See, e.g., H. Ansel et. al., Pharmaceutical Dosage Forms and Drug Delivery Systems (6th Ed. 1995) at pp. 196 and 1456-1457.

The term "color-body" means an impurity that imparts a color to a substance. Color-bodies may exist in amounts as low as a few parts per billion and still affect the color of a substance.

The term "prodrug" refers to compounds that undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances that are converted after administration to the actual substance which combines with receptors. The term prodrug is a generic term for agents, which undergo biotransformation prior to exhibiting their pharmacological action In some instances, preparation of SNAC may lead to a product which includes color-bodies. The creation of these color-bodies appears to not be pH dependent. In order to determine the identity of a color-body which leads to an observed pink color, a hydrolysis reaction was performed at reflux for an extended four day period of time. This yielded very pink SNAC free acid, which was dissolved in acetone and run through silica gel to achieve some separation of the impurity. The pink band was extracted into water and dried. This material was further separated by preparative high-performance liquid chromatography. The peak was determined to have a molecular weight of about 724, but the structure has not yet been elucidated. Applicants hypothesize that trace metals and/or oxygen are responsible for the formation of the pink color impurity. The success in avoiding the pink color using EDTA suggests that contaminating metal plays some role. Other anti-oxidants such as ascorbic acid (1%), NaHSO$_3$ (1%), PPh$_3$ (0.1%) are also effective at preventing the pink color formation. However, 2,6-di-tert-butyl-4-methylphenol (BHT) (1%) is not effective. De-gassing by vacuum and pressure N$_2$ three times are found to be inconsistent in avoiding the pink color. De-gassing by using boiled water is successful in avoiding the pink color In general, to form essentially pink-free SNAC free acid, 2,4-dioxo-1,3-benzoxazinyloctanoic acid ethyl ester can be reacted with sodium hydroxide (as a 40% aqueous solution) in water in the presence of EDTA, e.g., about 0.001 equivalent of EDTA, at elevated temperature, e.g., about 98° C. After the reaction is complete, the reaction mixture can be cooled to room temperature, and then can be charged to a different flask containing a premixed mixture of about 4 equivalents of HCl and acetone at 20° C. A solution of sodium hydroxide, e.g., 20% NaOH, can then be added to the resulting slurry can then added to adjust the pH to about 4.5. The slurry can then be heated, e.g., to about 60° C. for e.g., 0.5 hour and then can be subsequently cooled to room temperature and aged for, e.g., 4 hours. The slurry can then be filtered, washed with water, and dried in high vacuum at elevated temperature, e.g., about 80° C. to afford SNAC free acid.

Alternatively, the reaction can be run as above, but instead of using EDTA, ascorbic acid, NaHSO$_3$, or triphenylphosphine can be used. Also alternatively, the process water can be boiled prior to use in the hydrolysis reaction.

The invention thus provides new methods for synthesizing N-(8-[2-hydroxybenzoyl]-amino) caprylic acid while avoiding or reducing the production of a color-body impurity therein comprising the step of hydrolyzing 2,4-dioxo-1,3-benzoxazinyloctanoic acid ethyl ester by admixing 2,4-dioxo-1,3-benzoxazinyloctanoic acid ethyl ester with sodium hydroxide, water, and a member selected from the group consisting of ethylenediamine tetraacetic acid (EDTA), ascorbic acid, NaHSO$_3$, and triphenylphosphine to yield a reaction mixture.

The invention also provides methods for synthesizing N-(8-[2-hydroxy-benzoyl]-amino) caprylic acid while avoiding or reducing the production of a color-body impurity therein comprising the step of hydrolyzing 2,4-dioxo-1,3-benzoxazinyloctanoic acid ethyl ester by admixing 2,4-dioxo-1,3-benzoxazinyloctanoic acid ethyl ester with sodium hydroxide and previously boiled water to yield a reaction mixture.

In further embodiment, the methods set out above for the preparation of SNAC free acid also comprise the step of admixing acetone and hydrochloric acid with the reaction mixture.

To make SNAC sodium salt, SNAC free acid can be reacted with, e.g., about 1.02 equivalents of sodium hydroxide (as a 20% aqueous solution) in 2-propanol at about 40° C. After the addition is complete, the reaction mixture can be heated at, e.g., about 50° C., and cooled, e.g., to about 35° C., and can then be charged with seed crystal. After stirring at about 35° C. for about 1 hour, a suspension should form that can be slowly cooled to, e.g., about 30° C. and held at about 30° C. for about 1 hour to yield a thick suspension. Additional 2-propanol may be added at about 30° C., and the resulting slurry may then be cooled slowly to about 0° C. and aged for at least about 4 hours. The slurry can then be filtered, washed with mixed solvent of 2-propanol and water (about 10:1, v/v), and dried in high vacuum at about 90° C., to yield SNAC sodium salt with a monomodal particle size distribution.

Thus, the invention also provides methods for synthesizing N-(8-[2-hydroxy-benzoyl]-amino) caprylic acid sodium salt, comprising admixing N-(8-[2-hydroxy-benzoyl]-amino) caprylic acid suspended in 2-propanol with aqueous sodium hydroxide to form a solution of N-(8-[2-hydroxy-benzoyl]-amino) caprylic acid sodium salt. In particular, this method employs N-(8-[2-hydroxybenzoyl]-amino) caprylic acid that has been produced according to the methods of the present invention, so that the final N-(8-[2-hydroxybenzoyl]-amino) caprylic acid sodium salt product has reduced or absent color-body impurity.

In another embodiment, the method set out above for synthesizing N-(8-[2-hydroxybenzoyl]-amino) caprylic acid sodium salt includes the steps of adding additional 2-propanol to the solution of N-(8-[2-hydroxybenzoyl]-amino) caprylic acid sodium salt, seeding the solution of N-(8-[2-hydroxybenzoyl]-amino) caprylic acid sodium salt with crystalline N-(8-[2-hydroxybenzoyl]-amino) caprylic acid sodium salt to cause the dissolved N-(8-[2-hydroxybenzoyl]-amino) caprylic acid sodium salt to precipitate out of the solution, and then adding more 2-propanol to the solution, to yield SNAC sodium salt with a monomodal particle size distribution.

The present invention also provides solid pharmaceutical dosage forms for oral administration comprising a bisphosphonate, or a pharmaceutically acceptable salt thereof, which bisphosphonate is present in an amount not therapeutically effective when the bisphosphonate is orally administered alone; and SNAC, prepared according to the methods disclosed herein, which is present in an amount effective to facilitate absorption of the bisphosphonate in the gastrointestinal tract such that the bisphosphonate is therapeutically effective. The ratio of bisphosphonate to SNAC is from about 1:30 to about 1:1, respectively. These novel solid pharmaceutical dosage forms are useful in the treatment or control of bone diseases characterized by increased bone resorption, such as osteoporosis and hypercalcemia of cancer, as well as the treatment or control of pain that accompanies such disorders. The present invention also provides a method for treating such disorders employing the solid pharmaceutical dosage forms and a method for preparing the pharmaceutical dosage forms.

Oral administration of the bisphosphonate with the SNAC produced according to the invention described herein results in an increased bioavailability of the bisphosphonate compared to oral administration of the bisphosphonate alone, thereby enabling a lowering of the dose of the bisphosphonate while still achieving equivalent efficacy of the bisphosphonate. Oral administration of the bisphosphonate with the SNAC may result in a reduction of the approximately 2 hour period of fasting before taking the bisphosphonate and is expected to reduce the approximately 30-60 minute period of sitting or standing upright after taking the bisphosphonate.

As set out above, the present invention provides a novel solid pharmaceutical dosage form for oral administration comprising a bisphosphonate, or a pharmaceutically acceptable salt thereof, which bisphosphonate is present in an amount not therapeutically effective when the bisphosphonate is orally administered alone; and SNAC, or a pharmaceutically acceptable salt thereof, prepared according to the methods of the present invention, which SNAC is present in an amount effective to facilitate absorption of the bisphosphonate in the gastrointestinal tract such that the bisphosphonate is therapeutically effective. The ratio of bisphosphonate to SNAC is from about 1:30 to about 1:1, respectively. The dosage form may be administered to a mammal, e.g., a human.

The bisphosphonates in the present invention may be selected from a wide variety of bisphosphonates and pharmaceutically acceptable salts thereof. Bisphosphonates may be represented by the formula: $(HO)_2(O)P\text{—}C(R^1)(R^2)\text{-}P(O)(OH)_2$. In the above formula, $R^1$ may be selected from the group consisting of OH, Cl, and H; and $R^2$ may be selected from the group consisting of $(CH_2)_3NH_2$, Cl, $CH_2$-1-pyrrolidinyl, $CH_3$, $CH_2CH_2N(CH_3)(CH_2CH_2CH_2CH_2CH_3)$, N-cycloheptyl, H, $(CH_2)_5NH_2$, $(CH_2)_2N(CH_3)_2$, $(CH_2)_2NH_2$, $CH_2$-3-pyridinyl, S-4-chlorophenyl, $CH_2$-2-imidazo- pyridinyl, and $CH_2$-2-imidazolyl. Illustrative nonlimiting examples of bisphosphonates include alendronate [Fosamax®, $R^1$=OH, $R^2$=$(CH_2)_3NH_2$], clodronate [$R'$=Cl, $R^2$=Cl], EB-1053 [$R'$=OH, $R^2$=$CH_2$-1-pyrrolidinyl], etidronate [Didrocal®, $R^1$=OH, $R^2$=$CH_3$], ibandronate [Boniva®, $R^1$=OH, $R^2$=$CH_2CH_2N(CH_3)(CH_2CH_2CH_2CH_2CH_3)$], incadronate [$R'$=H, $R^2$=N-cycloheptyl], medronate [$R'$=H, $R^2$=H], neridronate [$R'$=OH, $R^2$=$(CH_2)_5NH_2$], olpadronate [$R'$=OH, $R^2$=$(CH_2)_2N(CH_3)_2$], pamidronate [Aredia®, $R^1$=OH, $R^2$=$(CH_2)_2NH_2$], risedronate [Actonel®, $R^1$=OH, $R^2$=$CH_2$-3-pyridinyl], tiludronate [Skelid®, $R^1$=H, $R^2$=S-4-chlorophenyl], YH529 [$R'$=OH, $R^2$=$CH_2$-2-imidazo-pyridinyl], and zoledronate [Zometa®, $R^1$=OH, $R^2$=$CH_2$-2-imidazolyl]. In particular, the bisphosphonate is alendronate or ibandronate, or a pharmaceutically acceptable salt thereof. Most particularly, the bisphosphonate is ibandronate, or a pharmaceutically acceptable salt thereof.

Ibandronate is disclosed in U.S. Pat. No. 4,927,814, which disclosure is incorporated herein by reference. Ibandronate may be represented by the following formula:

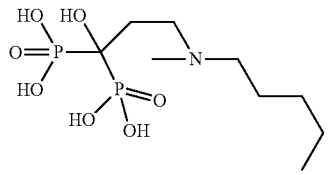 [SMILES: CCCCCN(C)CCC(O)(P(=O)(O)O)P(=O)(O)O]

Ibandronate is commercialized as the sodium salt, 3-(N-methyl-N-pentyl)-amino-1-hydroxypropane-1,1-diphosphonic acid, monosodium salt, monohydrate (Boniva®). Ibandronate has the molecular formula $C_9H_{22}NO_7P_2Na \cdot H_2O$ and a molecular weight of 359.24. Ibandronate sodium is a white- to off-white powder, which is freely soluble in water and practically insoluble in organic solvents.

The ratio of bisphosphonate to SNAC is such that absorption of the orally administered bisphosphonate in the gastrointestinal tract is facilitated over that of absorption of the bisphosphonate when orally administered alone. The ratio of bisphosphonate to SNAC according to the present invention may vary within limits. The ratio of bisphosphonate to SNAC may be adjusted to the requirements in each particular case including the particular bisphosphonate being administered, the particular SNAC being employed, the condition being treated, as well as the patient being treated.

The ratio of bisphosphonate to SNAC is preferably such that absorption of the orally administered bisphosphonate in the gastrointestinal tract is at least 2 times, preferably 3 times, more preferably 4 times, and most preferably 5 times greater than that of the bisphosphonate when orally administered alone. In general, in the case of oral administration to adult humans weighing approximately 70 Kg, the ratio of bisphosphonate to SNAC, as measured by weight of each compound as the free acid in the pharmaceutical composition, is from about 1:30 to about 1:1, preferably about 1:20, more preferably about 1:10, and most preferably about 1:5, respectively.

The therapeutically effective amount or dosage of bisphosphonate according to this invention can vary within wide limits. Such dosage will be adjusted to the individual requirements in each particular case including the condition being treated, the patient being treated, as well as the specific bisphosphonate being administered.

For example, the recommended oral dose of ibandronate for the treatment of osteoporosis, when administered alone, to adult humans weighing approximately 70 Kg is 2.5 mg once daily or 150 mg once monthly. In the present invention, the daily dose of ibandronate for the treatment of osteoporosis, when administered with SNAC, is lowered to from about 1.25 mg to about 0.25 mg, preferably from about 1 mg to about 0.4 mg, more preferably from about 0.65 mg to about 0.5 mg, and most preferably about 0.5 mg. The monthly dose of ibandronate for the treatment of osteoporosis, when administered with SNAC, is lowered to from about 75 mg to about 15 mg, preferably from about 60 mg to about 25 mg, more preferably from about 40 mg to about 30 mg, and most preferably about 30 mg.

The recommended oral dose of ibandronate for the treatment of hypercalcemia of cancer or the treatment of metastatic bone pain, when administered alone, to adult humans weighing approximately 70 Kg is 50 mg once daily. In the present invention, the daily dose of ibandronate for the treatment of hypercalcemia of cancer or the treatment of metastatic bone pain, when administered with SNAC, is lowered to from about 25 mg to about 5 mg, preferably from about 20 mg to about 8 mg, more preferably from about 13 mg to about 10 mg, and most preferably about 10 mg.

The anticipated oral dose of ibandronate for the treatment of hypercalcemia of cancer or the treatment of metastatic bone pain, when administered alone, to adult humans weighing approximately 70 Kg is 350 mg weekly. In the present invention, the anticipated weekly dose of ibandronate for the treatment of hypercalcemia of cancer or the treatment of metastatic bone pain, when administered with SNAC, is expected to be lowered to from about 175 mg to about 35 mg, preferably from about 140 mg to about 56 mg, more preferably from about 90 mg to about 70 mg, and most preferably about 70 mg.

The pharmaceutical dosage forms of the present invention may be prepared by simply admixing the bisphosphonate with the SNAC prior to administration. The dosage forms may also be prepared by admixing an aqueous solution of the bisphosphonate with the SNAC, just prior to administration. The solutions may optionally contain additives such as lactose monohydrate, croscarmellose sodium, povidone, water, sodium stearyl fumarate, and the like. Preferably, the solid pharmaceutical dosage form is prepared by intimately contacting the bisphosphonate with the SNAC.

The dosage forms are preferably in tablet or capsule form. In one embodiment, the dosage form is a tablet and includes povidone. In another embodiment, the dosage form is a capsule and includes povidone. Povidone is preferably present in the dosage form in an amount from about 2% to about 30%, preferably from about 10% to about 20%, most preferably from about 12% to about 15%, by weight of the total composition.

The SNAC may also be used to form microspheres containing the bisphosphonate. Microspheres are particularly useful for the oral administration of active agents, which do not pass, or only fractionally pass, through the gastrointestinal tract or are susceptible to chemical or enzymatic cleavage in the gastrointestinal tract. Methods for preparing microspheres are known and are disclosed, for example, in U.S. Pat. No. 5,650,386, which disclosure is incorporated herein by reference.

In another embodiment, the present invention provides a method for treating osteoporosis comprising orally administering to a subject, in need thereof, a novel solid pharmaceutical dosage form of the present invention. In yet another embodiment, the present invention provides a method for treating hypercalcemia of cancer comprising orally administering to a subject, in need thereof, a novel solid pharmaceutical dosage form of the present invention. In still yet another embodiment, the present invention provides a method for treating metastatic bone pain comprising orally administering to a subject, in need thereof, a novel solid pharmaceutical dosage form of the present invention. The dosage forms utilized in the aforementioned methods contain In still yet another embodiment, the present invention provides a method for preparing a solid pharmaceutical dosage form for oral administration comprising admixing:

(a) a bisphosphonate, or a pharmaceutically acceptable salt thereof, which bisphosphonate is present in an amount not therapeutically effective when the bisphosphonate is orally administered alone; and (b) SNAC prepared according to the methods of the present invention which is present in an amount effective to facilitate absorption of the bisphosphonate in the gastrointestinal tract such that the bisphosphonate is therapeutically effective;

where the ratio of bisphosphonate to SNAC is from about 1:30 to about 1:1, respectively.

The examples are presented for purposes of demonstrating, but not limiting, the methods of this invention.

EXAMPLES

Example 1

Production of SNAC Free Acid

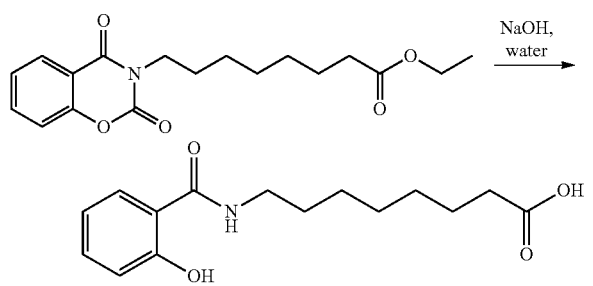

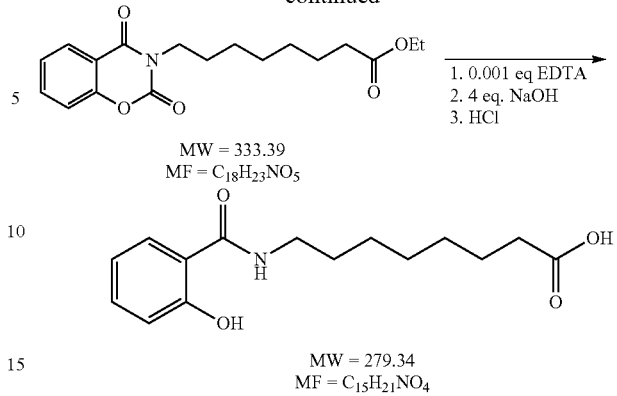

A dry, clean, 500 ml half jacketed, 4-neck round bottom flask, equipped with a mechanic stirrer, thermo couple, chiller, and an addition funnel, was charged with 153 g of water, 22 mg of EDTA (0.08 mmol), and 30 g of 2,4-dioxo-1,3-benzoazinyl-octanoic acid ethyl ester (76.49 mmol). The mixture was stirred for 30 minutes at 20±5° C. Then 29.22 g of 40% NaOH solution (292.18 mmol) was added to the mixture. The mixture was heated to ~97° C. and held for 20 hours. The mixture was then cooled to 20±5° C. The batch was charged to an addition funnel, and the flask was charged with 29 g of acetone and 36.25 g of 31% HCl. The batch in the first flask was transferred to the acetone/HCl solution over 40 minutes while maintaining temperature <30° C. After the transfer, the pH of the batch was adjusted to ~4.5 with 20% NaOH solution. The mixture was heated to ~60° C., held for 0.5 h, and then cooled to 20±5° C. The batch was held at 20±5° C. for at least 2 hours. The solid was filtered, washed with water, and dried at 80±5° C. under vacuum overnight to give 20.4 g (95% yield) of SNAC free acid.

Example 2

Formation of SNAC Sodium Salt

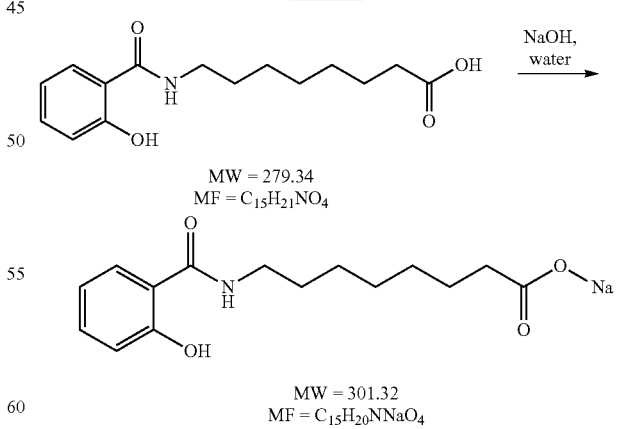

A 1 L, half jacketed, 4-neck round bottom flask equipped with a mechanical stirrer, a thermo couple, an additional funnel, and a condenser, was charged with 46.35 g of SNAC free acid (165.9 mmol), and 180 ml of iPrOH and stirred at room temperature (rt). The suspension was heated to 40° C.

To the resulting suspension was added 33.84 g of 20% NaOH (169.2 mmol) solution over a span of 30 minutes. The suspension has become a clear solution when about only half of the base was added. After the full amount of base was added, the clear solution was at pH=9.0. The reaction temperature was then raised to 50° C. and was stirred at 50° C. for 30 minutes. The almost colorless clear solution was cooled to 35° C. in one hour. The clear solution was then seeded with 100 mg of crystalline SNAC sodium salt (0.33 mol) and stirred at 35° C. for one hour. The clear solution has become a milky light suspension. The suspension was further cooled to 30° C. in one hour and hold at 30° C. for one hour, it has become a very thick white suspension. 180 ml of i-PrOH was added over a span of one hour. The internal temperature was kept at 30° C. through out the addition. The stirring actually became easier after the addition. The suspension was then cooled to 0° C. in a span of one hour and was aged at that temperature for 18 hours. The solid was filtered on a coarse sintered glass funnel and filtration was very fast. The solid was air-dried for one hour. The resulting white solid was transferred to a crystallization dish and was dried at 35° C. for 6 hours and at 90° C. with nitrogen bleeding for additional 18 hours. It was cooled in an oven to rt under vacuum (needs to be less than 40° C.) before removal from the oven. In total 46.8 g (93.6% yield) white solid was collected, which was found to by anhydrous SNAC sodium salt, with a monomodal particle size distribution. The water content was found to be 0.52%, as judged by Karl Fischer titration. The aqueous solution of the salt has pH=7.0. Water content needs to be carefully monitored during drying process to make sure the water level is below 1%, preferably below 0.5%. Before filtration, the reaction content may be aged at 0° C. overnight. No quality deterioration was observed. The anhydrous monomodal SNAC sodium salt product has good solubility in water, significantly higher than that of a trihydrate form.

The invention claimed is:

1. A method of making a compound of formula:

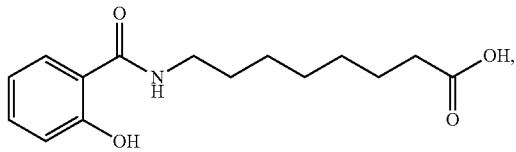 [SMILES: O=C(O)CCCCCCCNC(=O)c1ccccc1O]

or an anion or salt thereof, the method comprising the steps of:
i) preparing a reaction mixture comprising a compound of formula:

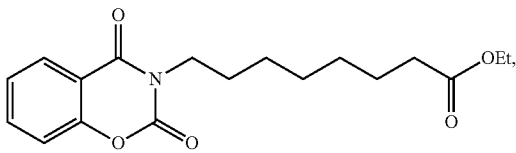 [SMILES: CCOC(=O)CCCCCCCn1c(=O)oc2ccccc2c1=O]

sodium hydroxide, and one or more of: ethylenediamine tetraacetic acid, ascorbic acid, NaHSO$_3$, and triphenylphosphine; and ii) generating a product mixture comprising an anion or a salt of a compound of formula:

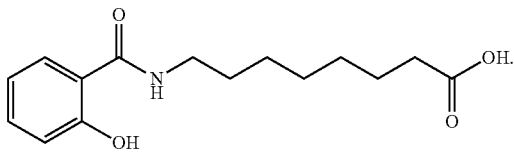 [SMILES: O=C(O)CCCCCCCNC(=O)c1ccccc1O]

2. The method of claim 1, wherein the reaction mixture, the product mixture, or both, further comprises water.

3. The method of claim 1, wherein the reaction mixture, the product mixture, or both, comprises ethylenediamine tetraacetic acid.

4. The method of claim 1, wherein the reaction mixture, the product mixture, or both, comprises ascorbic acid.

5. The method of claim 1, wherein the reaction mixture, the product mixture, or both, comprises NaHSO$_3$.

6. The method of claim 1, wherein the reaction mixture, the product mixture, or both, comprises triphenylphosphine.

7. The method of claim 1, further comprising heating the reaction mixture.

8. The method of claim 1, further comprising cooling the product mixture.

9. The method of claim 1, further comprising lowering the pH of the product mixture.

10. The method of claim 1, further comprising admixing acetone with the product mixture.

11. The method of claim 1, further comprising admixing HCl with the product mixture.

12. The method of claim 9, further comprising filtering a solid material from the product mixture, wherein the solid material comprises the compound of formula:

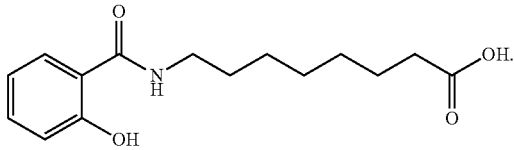 [SMILES: O=C(O)CCCCCCCNC(=O)c1ccccc1O]

13. The method of claim 12, further comprising washing the solid material with water.

14. The method of claim 12, further comprising drying the solid material.

* * * * *